(12) United States Patent
Anzalone et al.

(10) Patent No.: US 11,337,904 B2
(45) Date of Patent: May 24, 2022

(54) PERSONAL CARE COMPOSITIONS AND METHODS COMPRISING TRANS-1-CHLORO-3,3,3-TRIFLUOROPROPENE

(71) Applicant: HONEYWELL INTERNATIONAL INC., Morris Plains, NJ (US)

(72) Inventors: Anthony Anzalone, Angola, NY (US); Jon Thomas Herdlein, Buffalo, NY (US); Yiu Keung Ling, Amherst, NY (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

(21) Appl. No.: 16/230,202

(22) Filed: Dec. 21, 2018

(65) Prior Publication Data

US 2019/0201301 A1    Jul. 4, 2019

Related U.S. Application Data

(60) Provisional application No. 62/637,052, filed on Mar. 1, 2018, provisional application No. 62/611,246, filed on Dec. 28, 2017.

(51) Int. Cl.
| | |
|---|---|
| A61K 8/31 | (2006.01) |
| A61K 8/06 | (2006.01) |
| A61K 8/04 | (2006.01) |
| A61Q 19/00 | (2006.01) |
| A61K 8/69 | (2006.01) |
| A61Q 19/10 | (2006.01) |
| A61Q 5/02 | (2006.01) |

(52) U.S. Cl.
CPC .............. *A61K 8/315* (2013.01); *A61K 8/042* (2013.01); *A61K 8/046* (2013.01); *A61K 8/06* (2013.01); *A61K 8/69* (2013.01); *A61Q 19/00* (2013.01); *A61K 2800/87* (2013.01); *A61Q 5/02* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 6,737,041 | B1 | 5/2004 | Hussain |
| 10,435,342 | B2 | 10/2019 | Singh |
| 2006/0144864 | A1 | 7/2006 | Groys |
| 2012/0043492 | A1 | 2/2012 | Williams |
| 2012/0128964 | A1 | 5/2012 | Hulse |
| 2012/0237453 | A1 | 9/2012 | Tamarkin |
| 2014/0070129 | A1 | 3/2014 | Kennoy |
| 2017/0000713 | A1 | 1/2017 | Bakes |
| 2019/0117543 | A1* | 4/2019 | Zhao ................. A61K 8/20 |

FOREIGN PATENT DOCUMENTS

| | | |
|---|---|---|
| EP | 2336264 | 6/2011 |
| WO | 3185140 | 11/2001 |
| WO | 2018075864 | 4/2018 |

OTHER PUBLICATIONS

International Search Report in corresponding International Patent Application No. PCT/US2018/067878, dated Jan. 29, 2019, 11 pages.

* cited by examiner

*Primary Examiner* — Nannette Holloman
(74) *Attorney, Agent, or Firm* — Colleen D. Szuch

(57) ABSTRACT

Disclosed are personal care formulations, personal care methods and personal care devices that comprise or use a gel, lotion, cream or the like comprising (a) one or more active ingredients for providing a beneficial effect to the skin and/or hair and/or mucous membranes of a human and (b) from about 1 percent by weight to about 50 percent by weight of foam forming component(s) comprising trans-1-chloro-3,3,3-trifluoropropene (1233zd(E)).

18 Claims, 5 Drawing Sheets
(3 of 5 Drawing Sheet(s) Filed in Color)

PERSONAL CARE COMPOSITIONS AND METHODS COMPRISING TRANS-1-CHLORO-3,3,3-TRIFLUOROPROPENE

CROSS REFERENCE TO RELATED APPLICATIONS

The present application relates to and claims the priority benefit of US provisional application 62/637,052, filed Mar. 6, 2018, which is incorporated herein by reference in its entirety.

The present application relates to and claims the priority benefit of US provisional application 62/611,246, filed Dec. 28, 2017, which is incorporated herein by reference in its entirety.

FIELD OF THE INVENTION

The present invention relates to personal care compositions and to methods and devices for providing personal care, including but not limited to compositions, articles and methods that use post-foaming effects.

BACKGROUND

Personal care compositions, such as skin lotions and cleansers and shaving creams (including foams and gels), generally comprise several components in addition to the active ingredient. Such additional ingredients may include, for example, thickeners, suspending agents, surfactants and foaming agents, which are included in order to effect a property of the composition as it is being dispensed and/or upon application to the skin.

One particular type of formulation is a gel which is self-foaming either upon being dispensed and/or upon being rubbed into or onto the area of the skin or scalp being treated. For example, one of the more popular forms of personal care products used today is the post-foaming shave gel. In such post-foaming compositions, it is common to add soaps, surfactants, active ingredients and other components with relatively volatile hydrocarbons to form clear, stable gels or emulsions when kept under pressure. Once these materials are dispensed and mechanically agitated, the gels form foams, generally due to the post-dispensing addition of energy to the gel.

Applicants have come to appreciate that the performance of prior personal care formulations, including post-foaming and non post-foaming formulations, is lacking and/or could be improved in several respects. By way of example, applicants have found that in many prior formulations the volatile hydrocarbons that were heretofore used to form the foam in post-foam applications resulted in the degradation of other desirable aspects of the formulation. For example, applicants have come to appreciate that such prior post-foam formulations produced a foam too quickly after application, which tends to negate the ability of the formulation to spread on the skin or hair of the user, and/or to penetrate into the skin/hair to the extent that would be desirable to the user. Furthermore, even to the relatively small extent that prior post-foam formulations were able to spread on the skin prior to foaming, such formulations did not enhance or improve the ability of the active ingredient to penetrate into the pores of the skin and thereby provide both the perception and the actuality of improved performance.

Another aspect of prior formulations has been the ability to provide the user with the sensation of cooling as a result of application of the personal care product to the skin and/or hair. Such sensation has been provided in many prior formulations by the inclusion of certain ingredients known as sensates, which manipulate the transient receptor potential (TRP) channels contained in human tissue. See, for example, US 2017/0000713. Applicants have come to appreciate that the use of such sensate ingredients can have several disadvantages, including relatively high cost of these ingredients and their derivatives. Another potential disadvantage is the need for sensates to interact directly with the biological function of the user, which can be undesirable in certain cases/applications, such as users who may be especially sensitive to and/or allergic to the direct biological interaction and who might experience longer-lasting side effects as a result of the ingredient remaining in contact with the user. Accordingly, applicants have come to appreciate the desirability of achieving such a cooling sensation using a simpler and less costly mechanism and without the above-noted other disadvantages of sensates. Furthermore, applicants have come to appreciate the desire of many users to experience the cooling sensation that appears essentially immediately upon application to the skin/hair/mucous membrane, and these sensates have limited use in those skin, body and mucous membrane applications where an apparently instant refreshing cooling sensation is desired. Moreover, applicants have also come to appreciate the advantage of treatment compositions and methods in which the cooling effect is long lasting and preferably at the same time also being perceived to provide essentially immediate cooling sensation upon application.

BRIEF DESCRIPTION OF THE DRAWING

The patent or application file contains at least one drawing executed in color. Copies of this patent or patent application publication with color drawing(s) will be provided by the Office upon request and payment of the necessary fee.

SUMMARY

Figures 1A, 1B:
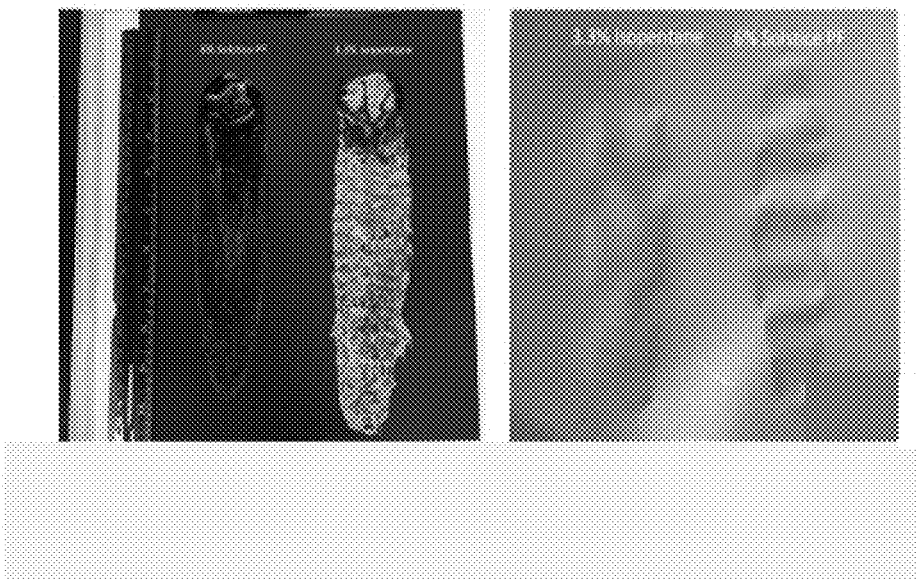
FIG. 1A is a black-and-white photograph showing the front view resulting from the experiment described in Example 3.
FIG. 1B is a black-and-white photograph showing the front view resulting from the experiment described in Example 3.

Applicants have come to appreciate that one or more of the disadvantages and failures described above in connection with prior formulations and methods, and preferably all of such disadvantages and failures, can be reduced or substantially eliminated using the methods, articles and personal care formulations according to the present invention.

The present invention includes methods of treating human skin, hair and/or mucous membranes comprising:

(a) providing a personal care composition in the form of a gel, lotion or cream or the like comprising: (i) one or more active ingredients; (ii) optionally but preferably one or more auxiliary gel, lotion or cream forming components; and (iii) foam forming component(s) comprising trans-1-chloro-3,3,3-trifluoropropene (1233zd(E));

(b) spreading said gel, lotion or cream on and/or into the skin, hair and/or mucous membrane of the human being treated; and (c) foaming said gel, lotion or cream during delivery and/or while in contact with the skin, hair and/or mucous membrane by evaporating said trans-1-chloro-3,3,3-trifluoropropene (1233zd(E)) from said gel, lotion or cream.

It will be appreciated by those skilled in the art that the ingredients that are used to form the gel, lotion or cream may themselves be considered to have an active function in the sense they provide a desired effect to the skin, hair or mucous membrane. By way of example, a skin conditioner may be in the form of a cream, which itself is considered to be an active ingredient of the formulation. Accordingly, the term "auxiliary gel, lotion or cream forming component" is used herein to identify ingredients which are included to in the formulation primarily for purposes other than improving the skin or hair, such as to impact the viscosity, feel, texture, delivery properties and the like of the formulation.

As used herein, the term "foaming said gel, lotion or cream" and similar terms mean that at least a substantial proportion of the gel, lotion, cream or the like is foamed. The term thus includes within its meaning steps in which some portion of the gel, lotion or cream remains unfoamed, although in preferred embodiments of the invention substantially all (e.g., 90% or more), of gel, lotion, cream or the like is foamed.

The present invention also includes methods of treating human skin, hair and/or mucous membranes comprising:

(a) providing a personal care composition in the form of a gel, lotion, cream or the like in a container, preferably a container under pressure, said gel, lotion or cream comprising: (i) one or more active ingredients; (ii) optionally but preferably one or more auxiliary gel, lotion or cream forming components; and (iii) foam forming component(s) comprising trans-1-chloro-3,3,3-trifluoropropene (1233zd(E));

(b) dispensing said gel lotion or cream from said container onto the skin, hair and/or mucous membrane of the human being treated;

(c) foaming said gel, lotion or cream by evaporating said trans-1-chloro-3,3,3-trifluoropropene (1233zd(E)) from said gel, lotion or cream; and (d) before, during and/or after said foaming step (c), spreading said gel, lotion, cream and/or foam on and/or into the skin, hair and/or mucous membrane of the human being treated.

The present invention also includes methods of treating human skin, hair and/or mucous membranes comprising:

(a) providing a personal care composition in the form of a gel, lotion, cream or the like comprising: (i) one or more active ingredients; (ii) optionally but preferably one or more auxiliary gel, lotion or cream forming components; and (iii) foam forming components comprising trans-1-chloro-3,3,3-trifluoropropene (1233zd(E)) and trans-1,3,3,3-tetrafluoropropene (1234ze (E));

(b) foaming said gel, lotion or cream by evaporating said trans-1-chloro-3,3,3-trifluoropropene (1233zd(E)) and/or said trans-1,3,3,3-tetrafluoropropene (1234ze (E)) from said gel, lotion or cream; and (c) before, during and/or after said foaming step (b), spreading said gel, lotion, cream and/or foam on and/or into the skin, hair and/or mucous membrane of the human being treated.

The present invention also includes methods of treating human skin, hair and/or mucous membranes comprising:

(a) providing a personal care composition in the form of a gel, lotion, cream or the like in a container, preferably a container under pressure, said gel, lotion or cream comprising: (i) one or more active ingredients; (ii) optionally but preferably one or more auxiliary gel, lotion or cream forming components; and (iii) foam forming components comprising trans-1-chloro-3,3,3-trifluoropropene (1233zd(E) and trans-1,3,3,3-tetrafluoropropene (1234ze (E));

(b) dispensing said gel, lotion or cream from said container onto the skin, hair and/or mucous membrane of the human being treated;

(c) during and/or after said dispensing step, foaming said gel lotion or cream by evaporating said trans-1-chloro-3,3,3-trifluoropropene (1233zd(E)) and/or trans-1,3,3,3-tetrafluoropropene (1234ze (E)) from said gel, lotion or cream; and (d) during and/or after said foaming step (c), spreading said gel, lotion or cream on and/or into the skin, hair and/or mucous membrane of the human being treated.

The present invention includes personal care formulations for treating human skin, hair and/or mucous membranes comprising a gel, lotion, cream or the like comprising:

(a) one or more active ingredients for providing a beneficial effect to the skin and/or hair of a human, (b) optionally but preferably one or more auxiliary gel, lotion or cream forming components, and (c) from about 1 percent by weight to about 50 percent by weight of foam forming component(s) comprising, consisting essentially of or consisting of trans-1-chloro-3,3,3-trifluoropropene (1233zd(E), said weight percentages being based on the total of components (a), (b) and (c) in the formulation. For the purposes of convenience personal care formulations according to this paragraph are sometimes referred to herein for convenience as Personal Care Formulation 2.

The present invention includes personal care formulations for treating human skin, hair and/or mucous membranes comprising a gel lotion, cream or the like comprising:

(a) one or more active ingredients for providing a beneficial effect to the skin and/or hair and/or mucous membranes of a human.

(b) optionally but preferably one or more auxiliary gel, lotion or cream forming components, and (c) from about 1 percent by weight to about 50 percent of foam forming components comprising trans-1-chloro-3,3,3-trifluoropropene (1233zd(E) and trans-1,3,3,3-tetrafluoropropene (1234ze (E)), wherein the weight ratio of said 1234ze(E) to said 1233zd(E) is from about 90:10 to about 50:50, said weight percentages being based on the total of components (a), (b) and (c) in the formulation. For the purposes of convenience personal care formulations according to this paragraph are sometimes referred to herein for convenience as Personal Care Formulation 2.

The present invention includes personal care formulations for treating human skin, hair and/or mucous membranes comprising a gel, lotion, cream or the like comprising:

(a) one or more active ingredients for providing a beneficial effect to the skin and/or hair and/or mucous membranes of a human, (b) optionally but preferably one or more auxiliary gel, lotion or cream forming components, and (c) from about 1 percent by weight to about 10 percent of foam forming components comprising trans-1-chloro-3,3,3-trifluoropropene (1233zd(E), said weight percentages being based on the total of components (a), (b) and (c) in the formulation. For the purposes of convenience personal care formulations according to this paragraph are sometimes referred to herein for convenience as Personal Care Formulation 3.

The present invention includes personal care formulations for treating human skin, hair and/or mucous membranes comprising a gel, lotion, cream or the like comprising:

(a) one or more active ingredients for providing a beneficial effect to the skin and/or hair and/or mucous membranes of a human.

(b) optionally but preferably one or more auxiliary gel, lotion or cream forming components, and (c) from about 1 percent by weight to about 10 percent of foam forming components consisting essentially of trans-1-chloro-3,3,3-trifluoropropene (1233zd(E), said weight percentages being based on the total of components (a), (b) and (c) in the formulation. For the purposes of convenience personal care formulations according to this paragraph are sometimes referred to herein for convenience as Personal Care Formulation 4.

The present invention includes personal care formulations for treating human skin, hair and/or mucous membranes comprising a gel lotion, cream or the like comprising:

(a) one or more active ingredients for providing a beneficial effect to the skin and/or hair and/or mucous membranes of a human.

(b) optionally but preferably one or more auxiliary gel, lotion or cream forming components, and (c) from about 1 percent by weight to about 10 percent of foam forming components consisting of trans-1-chloro-3,3,3-trifluoropropene (1233zd(E), said weight percentages being based on the total of components (a), (b) and (c) in the formulation. For the purposes of convenience personal care formulations according to this paragraph are sometimes referred to herein for convenience as Personal Care Formulation 5.

The present invention includes personal care formulations for treating human skin, hair and/or mucous membranes comprising a gel, lotion, cream or the like comprising:

(a) one or more active ingredients for providing a beneficial effect to the skin and/or hair and/or mucous membranes of a human.

(b) optionally but preferably one or more auxiliary gel, lotion or cream forming components, and (c) from about 3 percent by weight to less than about 10 percent of foam forming components comprising trans-1-chloro-3,3,3-trifluoropropene (1233zd(E), said weight percentages being based on the total of components (a), (b) and (c) in the formulation. For the purposes of convenience personal care formulations according to this paragraph are sometimes referred to herein for convenience as Personal Care Formulation 6.

The present invention includes personal care formulations for treating human skin, hair and/or mucous membranes comprising a gel, lotion, cream or the like comprising:

(a) one or more active ingredients for providing a beneficial effect to the skin and/or hair and/or mucous membranes of a human.

(b) optionally but preferably one or more auxiliary gel, lotion or cream forming components, and (c) from about 3 percent by weight to about 6 percent of foam forming components consisting essentially of trans-1-chloro-3,3,3-trifluoropropene (1233zd(E), said weight percentages being based on the total of components (a), (b) and (c) in the formulation. For the purposes of convenience personal care formulations according to this paragraph are sometimes referred to herein for convenience as Personal Care Formulation 7.

The present invention includes personal care formulations for treating human skin, hair and/or mucous membranes comprising a gel, lotion, cream or the like comprising:

(a) one or more active ingredients for providing a beneficial effect to the skin and/or hair and/or mucous membranes of a human, (b) optionally but preferably one or more auxiliary gel, lotion or cream forming components, and (c) from about 3 percent by weight to about 6 percent of foam forming components consisting of trans-1-chloro-3,3,3-trifluoropropene (1233zd(E), said weight percentages being based on the total of components (a), (b) and (c) in the formulation. For the purposes of convenience personal care formulations according to this paragraph are sometimes referred to herein for convenience as Personal Care Formulation 8.

The present invention also includes a personal care formulation in the form of an emulsion and/or dispersion comprising:

(i) one or more active ingredients for providing a beneficial effect to the skin and/or hair of a human, (ii) optionally but preferably one or more auxiliary gel, lotion or cream forming components, (iii) foam forming component(s) present in an amount of from about 30 percent by weight to about 50 percent by weight based on the total weight of the components (i), (ii) and (iii), said foam forming component(s) comprising, consisting essentially of or consisting of:

(1) from about 5 percent to about 50 percent by weight, based on the total of components (1) and (2), of trans-1-chloro-3,3,3-trifluoropropene (1233zd(E)); and (2) from about 50 percent to about 95 percentage by weight, based on the total of components (1) and (2), of trans-1,3,3,3-tetrafluoropropene (1234ze (E)).

For the purposes of convenience personal care formulations according to this paragraph are sometimes referred to herein for convenience as Personal Care Formulation 9.

The present invention also includes a personal care formulation in the form of an emulsion and/or dispersion comprising:

(i) one or more active ingredients for providing a beneficial effect to the skin and/or hair of a human, (ii) optionally but preferably one or more auxiliary gel, lotion or cream forming components.

(iii) foam forming component(s) present in an amount of from about 30 percent by weight to about 50 percent by weight based on the total weight of the components (i), (ii) and (iii), said foam forming component(s) comprising, consisting essentially of or consisting of:

(1) from about 15 percent to about 40 percent by weight, based on the total of components (1) and (2), of trans-1-chloro-3,3,3-trifluoropropene (1233zd(E)); and (2) from about 60 percent to about 85 percentage by weight, based on the total of components (1) and (2), of trans-1,3,3,3-tetrafluoropropene (1234ze (E)).

For the purposes of convenience personal care formulations according to this paragraph are sometimes referred to herein for convenience as Personal Care Formulation 10.

The present invention includes methods of treating human skin, hair and/or mucous membranes comprising applying to the human skin, hair and/or mucous membranes a personal care composition of the present invention, including each of Personal Car Formulations 1-10.

The present invention includes methods of treating human skin, hair and/or mucous membranes comprising spreading on the human skin, hair and/or mucous membranes a personal care composition of the present invention, including each of Personal Car Formulations 1-10.

The present invention includes methods of treating human skin, hair and/or mucous membranes comprising delivering to the human skin, hair and/or mucous membranes a personal care composition of the present invention, including each of Personal Car Formulations 1-10, and then foaming the delivered personal care composition.

The present invention includes methods of treating human skin, hair and/or mucous membranes comprising delivering to the human skin, hair and/or mucous membranes a personal care composition of the present invention, including each of Personal Car Formulations 1-10, and then foaming the delivered personal care composition by evaporation of said form forming component.

The present invention includes methods of treating human skin, hair and/or mucous membranes comprising: (a) providing a personal care composition comprising one or more active ingredients and trans-1-chloro-3,3,3-trifluoropropene (1233zd(E)), where said one or more active ingredients are carried by and/or with said 1233zd(E);
(b) applying said personal care composition on and/or into the skin, hair and/or mucous membrane of the human being treated; and
(c) evaporating said trans-1-chloro-3,3,3-trifluoropropene (1233zd(E)) from said applied personal care composition whereby at least a portion of said one or more active ingredients remains on and/or in the skin, hair and/or mucous membrane of the human being treated during said evaporation and whereby upon said evaporation said human being treated experiences a cooling sensation.

As used herein, the term "evaporating said trans-1-chloro-3,3,3-trifluoropropene (1233zd(E))" and similar terms mean that at least a substantial proportion of the 1233zd is evaporated. The term thus includes within its meaning steps in which some portion of 1233zd remains unevaporated, although in preferred embodiments of the invention substantially all (e.g., 90% or more), of the 1233zd is evaporated. It will also be appreciated that the requirement that said one or more active ingredients remains on and/or in the skin, hair and/or mucous membrane of the human being treated contemplates both "stay on" compositions and methods and "rinse off" compositions and methods. Thus, the present invention includes methods in which the active ingredient is intended to remain on the skin, hair, and/or mucous membrane of the use without active intention or effort of the user to remove the product. In such "leave on" applications it is preferred that the substantially all of the 1233zd will be evaporated over a substantial period of time (e.g., 5 minutes or more) after application. On the other hand, in "rinse off" applications it is contemplated that an affirmative action will be taken to remove the cream, lotion, gel, foam or the like after application (such as by rinsing with water for example), and in such an embodiment it is contemplated that some portion, and potentially a substantial portion of the 1233zd will be removed from the user prior to evaporation. Thus, both "stay on" and "rinse off" applications are within the scope of the present invention.

The present invention includes methods of treating human skin, hair and/or mucous membranes comprising:
(a) providing a personal care composition comprising one or more active ingredients and from about 1 percent by weight to about 50 percent by weight of trans-1-chloro-3,3,3-trifluoropropene (1233zd(E)), where said one or more active ingredients are carried by and/or with said 1233zd(E) and wherein said weight percentages are based on the total of the components in the personal care composition;
(b) applying said personal care composition on and/or into the skin, hair and/or mucous membrane of the human being treated; and
(c) evaporating said trans-1-chloro-3,3,3-trifluoropropene (1233zd(E)) from said applied personal care composition whereby at least a portion of said one or more active ingredients remains on and/or in the skin, hair and/or mucous membrane of the human being treated during said evaporation and whereby upon said evaporation said human being treated experiences a cooling sensation.

The present invention includes methods of treating human skin, hair and/or mucous membranes comprising:
(a) providing a personal care composition comprising one or more active ingredients and from about 1 percent by weight to about 50 percent by weight of a combination of trans-1-chloro-3,3,3-trifluoropropene (1233zd(E)) and trans-1,3,3,3-tetrafluoropropene (1234ze (E)), wherein: (i) the weight ratio of said 1234ze(E) to said 1233zd(E) is from about 90:10 to about 50:50; (ii) said one or more active ingredients are carried by and/or with at least one of said 1233zd(E) and said 1234ze(E); and (iii) wherein said weight percentages are based on the total of the components in the personal care composition;
(b) applying said personal care composition on and/or into the skin, hair and/or mucous membrane of the human being treated; and
(c) evaporating said trans-1-chloro-3,3,3-trifluoropropene (1233zd(E)) from said applied personal care composition whereby at least a portion of said one or more active ingredients remains on and/or in the skin, hair and/or mucous membrane of the human being treated during said evaporation and whereby upon said evaporating said human being treated experiences a cooling sensation.

The present invention includes articles for applying personal care formulations for treating human skin, hair and/or mucous membranes comprising a gel, lotion, cream or the like, said article comprising:
(a) a closed container being openable to dispensing the contents thereof;
(b) a personal care formulation contained within said container, said personal care formulation comprising:
(i) one or more active ingredients for providing a beneficial effect to the skin and/or hair of a human,
(ii) optionally but preferably one or more auxiliary gel, lotion or cream forming components.
(iii) from about 1 percent by weight to about 50 percent by weight of foam forming component(s) comprising, consisting essentially of or consisting of trans-1-chloro-3,3,3-trifluoropropene (1233zd(E), said weight percentages being based on the total of components (i), (ii) and (iii) in the formulation; and
(c) optionally an external propellant for providing a force tending to eject said personal care composition from said container.

Those skilled in the art will appreciate that the articles of the present invention include a closed container which is openable to dispense the personal care composition of the present invention. The invention thus includes containers in which the container is openable but not readily re-closed (such as would be the case of a sachet or the like which may be torn or ripped to provide an opening for dispensing the personal care formulation) and containers which are re-closable (such as would be the case of can or the like which has a nozzle with a valve that can be opened to allow dispensing of the personal care formulation and then re-closed to maintain the remaining portion of the formulation in the can for use at a later time.) In either case, but primarily in the case of a re-closable container, it is contemplated that the foaming component(s) of the present invention may also provide a force tending to expel the personal care formulation from the container. By way of example, in preferred embodiments in which the foaming component comprises both 1233zd and 1234ze, the 1234ze component of the personal care composition will generally exit the container with the formulation and serve not only to provide a foaming action but will also serve to at least assist in expelling the personal care formulation from the container. In such embodiments, the formulation preferably includes both the 1233zd(E) and the 1234ze(E) as components that are miscible with and/or dispersed in and/or emulsified with the formulation, and in such a case, the 1234ze(E) component would contribute to foaming of the formulation as it exits the container as well as providing a propelling force. For the purposes of the description of the present invention, 1234ze in such embodiments, and other components which behave in the same or similar manner, are within the term "foaming component(s)" and the like since it contributes substantially to foaming of the personal care composition. It is contemplated that in other embodiments 1234ze, or other materials having a relatively high vapor pressure, may be included in the container in such a way that they operate to help propel the personal care composition from the container but do not contribute substantially to foaming. Such embodiments may include, for example, providing a bag-on-valve type of arrangement in which the personal care composition of the present invention is contained within a bag within the container and 1234ze is contained in the container but outside of the bag and thus exerts an expelling force on the personal care composition by exerting a pressure on the bag. (See for example US 20130184233, which is incorporated herein by reference). In such a case, the 1234ze that is outside of the bag is termed herein as an "external propellant." In other embodiments, a propellant is included in the can but remains mostly separated from the present personal care composition such as, for example, by being phase-separated from the personal care composition, and in such an embodiment propellant tends to remain in the can as the personal care formulation is expelled. In such embodiments the phase-separated propellant would be considered an "external propellant" since it would not contribute substantially to foaming of the personal care composition. All of such embodiments are within the scope of the present invention.

Accordingly, the present invention includes articles for applying personal care formulations for treating human skin, hair and/or mucous membranes comprising a gel, lotion, cream or the like, said article comprising:
(a) a closed container being openable to dispensing the contents thereof;
(b) a personal care formulation contained within said container, said personal care formulation being in the form of an emulsion and/or dispersion comprising:
(i) one or more active ingredients for providing a beneficial effect to the skin and/or hair of a human,
(ii) optionally but preferably one or more auxiliary gel, lotion or cream forming components.
(iii) foam forming component(s) present in an amount of from about 30 percent by weight to about 50 percent by weight based on the total weight of the components (i), (ii) and (iii), said foam forming component(s) comprising, consisting essentially of or consisting of:
(1) from about 5 percent to about 50 percent by weight, based on the total of components (1) and (2), of trans-1-chloro-3,3,3-trifluoropropene (1233zd(E)); and
(2) from about 50 percent to about 95 percentage by weight, based on the total of components (1) and (2), of trans-1,3,3,3-tetrafluoropropene (1234ze (E)); and
(c) optionally an external propellant for providing a force tending to eject said personal care composition from said container.

Accordingly, the present invention includes articles for applying personal care formulations for treating human skin, hair and/or mucous membranes comprising a gel, lotion, cream or the like, said article comprising:
(a) a closed container being openable to dispensing the contents thereof;
(b) a personal care formulation contained within said container, said personal care formulation being in the form of an emulsion and/or dispersion comprising:
(i) one or more active ingredients for providing a beneficial effect to the skin and/or hair of a human.
(ii) optionally but preferably one or more auxiliary gel, lotion or cream forming components.
(iii) foam forming component(s) present in an amount of from about 30 percent by weight to about 50 percent by weight based on the total weight of the components (i), (ii) and (iii), said foam forming component(s) comprising, consisting essentially of or consisting of:
(1) from about 15 percent to about 40 percent by weight, based on the total of components (1) and (2), of trans-1-chloro-3,3,3-trifluoropropene (1233zd(E); and
(2) from about 60 percent to about 85 percentage by weight, based on the total of components (1) and (2), of trans-1,3,3-tetrafluoropropene (1234ze (E)); and
(c) optionally an external propellant for providing a force tending to eject said personal care composition from said container.

The present invention also includes methods of treating human skin, hair and/or mucous membranes with a personal care gel, lotion, cream, foam or the like, said method comprising:
(a) providing a closed container openable to dispensing the contents thereof and including therein a personal care formulation in the form of an emulsion and/or dispersion comprising:
(i) one or more active ingredients for providing a beneficial effect to the skin and/or hair of a human.
(ii) optionally but preferably one or more auxiliary gel, lotion or cream forming components,
(iii) foam forming component(s) present in an amount of from about 30 percent by weight to about 50 percent by weight based on the total weight of the components (i), (ii) and (iii), said foam forming component(s) comprising, consisting essentially of or consisting of:
(1) from about 5 percent to about 50 percent by weight, based on the total of components (1) and (2), of trans-1-chloro-3,3,3-trifluoropropene (1233zd(E)); and
(2) from about 50 percent to about 95 percentage by weight, based on the total of components (1) and (2), of a co-foaming agent different than said 1233zd(E), said co-foaming agent preferably comprising, consisting of or consisting of trans-1,3,3,3-tetrafluoropropene (1234ze (E)); and
(iv) optionally an external propellant for providing a force tending to eject said personal care composition from said container.

(b) dispensing said personal care formulation from said container by substantially simultaneously propelling said personal care formulation from said container and initially foaming said personal care formulation, whereby said propelling and initial foaming is provided by said co-foaming agent;
(c) applying said dispensed personal care formulation to the skin, hair and/or mucous membranes in the form of a foam; and
(d) providing a cooling sensation to the human being treated by evaporating at least a portion said trans-1-chloro-3,3,3-trifluoropropene (1233zd(E)) from said applied personal care composition after said applying step.

The present invention also includes methods of treating human skin, hair and/or mucous membranes with a personal care gel lotion, cream, foam or the like, said method comprising:
(a) providing a closed container openable to dispensing the contents thereof and including therein a personal care formulation in the form of an emulsion and/or dispersion comprising:
(i) one or more active ingredients for providing a beneficial effect to the skin and/or hair of a human,
(ii) optionally but preferably one or more auxiliary gel, lotion or cream forming components.
(iii) foam forming component(s) present in an amount of from about 30 percent by weight to about 50 percent by weight based on the total weight of the components (i), (ii) and (iii), said foam forming component(s) comprising, consisting essentially of or consisting of:
(1) from about 15 percent to about 40 percent by weight, based on the total of components (1) and (2), of trans-1-chloro-3,3,3-trifluoropropene (1233zd(E)); and
(2) from about 60 percent to about 85 percentage by weight, based on the total of components (1) and (2), of a co-foaming agent different than said 1233zd(E), said co-foaming agent preferably comprising, consisting of or consisting of trans-1,3,3,3-tetrafluoropropene (1234ze (E)); and
(iv) optionally an external propellant for providing a force tending to eject said personal care composition from said container,
(b) dispensing said personal care formulation from said container by substantially simultaneously propelling said personal care formulation from said container and initially foaming said personal care formulation, whereby said propelling and initial foaming is provided by said co-foaming agent;
(c) applying said dispensed personal care formulation to the skin, hair and/or mucous membranes in the form of a foam; and
(d) providing a cooling sensation to the human being treated by evaporating at least a portion said trans-1-chloro-3,3,3-trifluoropropene (1233zd(E)) from said applied personal care composition after said applying step.

The present invention also includes methods of treating human skin, hair and/or mucous membranes with a personal care gel, lotion, cream, foam or the like, said method comprising:
(a) providing a closed container openable to dispensing the contents thereof and including therein a personal care formulation in the form of an emulsion and/or dispersion comprising:
(i) one or more active ingredients for providing a beneficial effect to the skin and/or hair of a human.
(ii) optionally but preferably one or more auxiliary gel, lotion or cream forming components,
(iii) foam forming component(s) present in an amount of from about 30 percent by weight to about 50 percent by weight based on the total weight of the components (i), (ii) and (iii), said foam forming component(s) comprising, consisting essentially of or consisting of:
(1) from about 15 percent to about 40 percent by weight, based on the total of components (1) and (2), of trans-1-chloro-3,3,3-trifluoropropene (1233zd(E)); and
(2) from about 60 percent to about 85 percentage by weight, based on the total of components (1) and (2), of a co-foaming agent different than said 1233zd(E), said co-foaming agent preferably comprising, consisting of or consisting of trans-1,3,3,3-tetrafluoropropene (1234ze (E)); and
(iv) optionally an external propellant for providing a force tending to eject said personal care composition from said container,
(b) dispensing said personal care formulation from said container by substantially simultaneously propelling said personal care formulation from said container and initially foaming said personal care formulation, whereby said propelling and initial foaming is provided by said co-foaming agent;
(c) applying said dispensed personal care formulation to the skin, hair and/or mucous membranes in the form of a foam; and
(d) providing a cooling sensation to the human being treated by evaporating at least a portion said trans-1-chloro-3,3,3-trifluoropropene (1233zd(E)) from said applied personal care composition after said applying step wherein at least a portion of said one or more active ingredients remains on and/or in the skin, hair and/or mucous membrane of the human being treated during said evaporation.

DETAILED DESCRIPTION

The preferred methods, articles and compositions of the present invention provide one or more, and preferably several, unexpected performance properties compared to prior personal care methods and personal care compositions. These performance advantages include:
improved spreadability
improved wettability
improved penetration of the active ingredient into the skin, hair and/or mucous membrane of the user
cooling sensation to the skin/mucous membrane that is or at least is perceived to be felt essentially immediately upon application
enhanced and long lasting cooling sensation provided to the user, preferably without the use of sensates.

As used herein, the terms "personal care composition," personal care formulation" and the like means compositions, formulations and the like that are to be topically applied to a person.

The personal care compositions and formulations of the present invention can be in the form, for example, of lotions, creams, gels and the like, and in each of such forms the composition is preferably a post-foaming composition or formulation. It will be appreciated, therefore, that while post-foaming formulation are preferred in many applications, lotions, creams, gels and the like that are not post-foaming are also within the broad scope of the present invention, including particularly embodiments which provide cooling sensation to the user. The compositions and formulations of the present invention can be in the form of sprayed or aerosolized powders, mists and the like which generally are not post-foaming compositions but which provide the advantageous cooling sensation of the present invention.

As used herein, the term "post-foaming" refers to gels, creams, lotions and the like which as applied are essentially not in the form of a foam but which as a result of the application of heat (which may be in the form of body heat) or other energy (such as kinetic energy associated with rubbing or spreading the formulation on the skin and/or in the hair, for example) produce a foamed product. For the purposes of convenience, but not necessarily by way of limitation, compositions, formulations and methods associated with post-foaming action are described below separately from non-post foaming compositions, formulations and methods.

Post-Foaming Compositions, Formulations and Methods

The post-foaming aspects of the present invention can utilize formulations and compositions in the form of lotions, creams, gels and the like, with gels being preferred. In such embodiments the formulations and compositions generally comprise: (a) one or more active components, preferably comprising a cleanser; (b) optionally but preferably one or more auxiliary components which help to form the cream, lotion or gel and/or which help to form the body of the foam; (c) a foaming agent comprising, or consisting essentially of, or consisting of trans-1-chloro-3,3,3-trifluoropropene (1233zd(E); and (d) optional additional components other than components (a), (b) and (c) that may be included in the composition.

For the purpose of convenience, but not by way of limitation, the components (a), (b) and (d) are sometimes referred to herein as the "formulation base," or the "cleanser base" (in the case where the active component includes a cleanser) or the "gel base" (in the case where the formulation is in the form of a gel).

Active Components

The active component(s) used in the compositions and methods of the present invention can have a wide variety of purposes and functions, and all such components are within the scope of the present invention. In general, such components will provide or at least be expected to provide some benefit to the user, preferably to the skin, hair and/or mucous membrane of the user. Thus, the active components can include cosmetic agents (that is, agents that are cosmetically treating, providing nutrition to and/or conditioning the skin, hair or mucous membrane via topical application), medicinal agents (that is, agents that capable of promoting or assisting in the recovery from injury or illness, preferably to the skin, hair or mucous membrane), and pharmaceutical agents (that is, drugs that are appropriate for delivery by topical application, including preferably drugs that are effective at treating skin, hair and mucous membranes). It will be appreciate by those skilled in the art that active ingredients can have more than one mode of operation and/or effect and therefore may be properly included in two or more categories of product for the purposes of the present invention.

Examples of active components include but are not limited to: coloring, de-coloring and appearance altering agents (such as pigments, depigmentation agents, skin lighteners, reflectants and the like); hair treatment agents (such as shaping agents, detangling agents, wet combing agents, anti-hair loss agents, hair growth promoting agents, hair growth inhibitors, hair colorants, hair conditioners, hair softeners; hair moisturizers, anti-dandruff agents and the like); film forming polymers; humectants; amino acids and their derivatives; antimicrobial agents; allergy inhibitors; anti-acne agents (such as salicylic acid, benzoyl peroxide, sulfur, adapalene and glycolic acid); anti-aging and anti-wrinkling agents (such as dimethylaminoethanol ("DMAE"), retinol, Vitamin C, hydroxy acids, peptides, tea extracts, grape seed extracts and niacinamide), antiseptics; analgesics; antitussives; anti-pruritics; local anesthetics; antihistamines; anti-infective; inflammation inhibitors; deodorants and anti-perspirants (aluminium chlorohydrate and aluminium-zirconium tetrachlorohydrate); medicament agents; skin emollients and skin moisturizers; skin firming agents; anti-fungal agents; shaving preparations, lotions, creams and gels; perfumes; make-up preparations; cosmetics (such as skin cleansers, skin conditioners, make-up and the like); and sun screen and sun blocks (such as benzophenones, bornelone, butyl paba, cinnamidopropyl trimethyl ammonium chloride, disodium distyrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate 0, and red petrolatum); insect repellants, skin protectants (such as atmeal, betaglucan, feverfew, soy and derivatives thereof, bicarbonate of soda, colloidal oatmeal, surfactant based colloidal oatmeal cleanser, *Anagallis Arvensis, Oenothera Biennis, Verbena Officinalis*, and the like), vitamins (such as vitamin B complex; including thiamine, nicotinic acid, biotin, pantothenic acid, choline, riboflavin, vitamin B6, vitamin B12, pyridoxine, inositol, carnitine; vitamins A, C, D, E, K and their derivatives such as vitamin A palmitate and pro-vitamins, e.g. (i.e. panthenol (pro vitamin B5) and panthenol triacetate).

The amount of the active component(s) to be used with the present invention can vary widely depending on the particular application, and all such amounts can be determined by those skilled in the art in view of the teachings contained herein and are within the broad scope of the invention. For example, amount of the active component(s) may vary depending upon the ability of the component to penetrate through, onto, or into the pores of the skin, hair or mucous membrane, in view of the enhancements thereto provided by the present invention. Other factors which may influence the relative amount of the active component include the particular active component involved, the particular benefit desired, the sensitivity of the user to the active component, the health condition, age, and skin, hair, and/or mucous membrane condition of the user, and the like. In sum, the benefit agent is preferably used in a "safe and effective amount," which is an amount that is high enough to deliver a desired skin, hair or mucous membrane benefit or to modify a certain condition to be treated and which avoids unwanted deleterious serious side effects. In preferred embodiments, the active components together are present in the personal care composition or personal care formulation system in an amount, based upon the total weight of the composition/formulation, of from about 0.01 percent to about 50 percent by weight, or from about 0.01 percent to about 20 percent, or from about 0.01 percent to about 10 percent or from about 0.01 percent to about 5 percent, or from about 0.01 percent to about 1.0 percent by weight.

Auxiliary Gel, Lotion or Cream Forming Components

The types of auxiliary components that may be used in the formulations of the present invention can vary widely depending on the particular form of the formulation (e.g., gel, cream or lotion) and the particular attributes of the formulation desired, and any and all such components are included within the scope of the present invention.

In connection with gels, for example, the gel forming component in preferred embodiments comprises, preferably in major proportion based on the total weight of the formulation, an aqueous soap. The soap in the aqueous soap component can be, for example, either a soap or a surface active agent, which is also sometimes called a wetting agent, which is generally anionic or nonionic in character.

The soaps (water soluble salts of higher fatty acids) which are preferably amine or basic salts, that suitable for the production of a post-foaming gel are generally known in the art, and all such soaps are within the scope of the present invention. In general, such a component can preferably be an alkali, ammonium or soluble amine salt of a fatty acid such as stearic acid, palmitic acid, myristic acid and the like. As known in the art, soaps may also be prepared by neutralization or saponification of animal fats, such as tallow or vegetable fats. The selection of a suitable soap component is deemed to be within the scope of those skilled in the art from the teachings herein.

The anionic or nonionic surface active agent which can be employed instead of a soap, or in conjunction therewith, should be one which is appreciably soluble in water, and as examples of such agents there may be mentioned triethanolamine lauryl sulfate, sodium lauryl sulfate, sodium dodecyl benzene sulfonate, water-soluble polyoxyethylene ethers of alkyl-substituted phenols and water-soluble polyoxyethylene cetyl ethers. The selection of a suitable wetting agent is deemed to be within the scope of those skilled in the art from the teachings herein.

It has been acknowledged that one difficulty associated with the formation of gels for use in post-foaming applications is the difficulty of forming a gel that in its unfoamed state is not easily spreadable over the skin or hair in an even and fluid manner. See, for example, U.S. Pat. No. 5,334,325, which describes the use of particular alkoxylated alkyl phosphate ester surfactant surfactants, the contents of which are incorporated herein by reference.

Other auxiliary ingredients that may be included in the present gels, creams and lotions for use in post-foaming applications include polymers for gel thickening and lubrication, cosmetic esters for emolliency, humectants for moisturization, fragrances, dyes and preservatives.

The amount of the auxiliary component(s) to be used with the present invention can vary widely depending on the particular application, and all such amounts can be determined by those skilled in the art in view of the teachings contained herein and are within the broad scope of the invention. In preferred embodiments, the auxiliary component(s) together are present in the personal care composition or personal care formulation system in an amount, based upon the total weight of the composition/formulation, of from about 40 percent to about 90 percent by weight, or from about 50 percent to about 80 percent by weight, or from about 50 percent to about 70 percent by weight, based on the total weight of the components in formulation.

Foaming Agents

As mentioned above, the foaming agent for use in the present formulations and methods comprises 1-chloro-3,3,3-trifluoropropene (1233zd). Although it is contemplated that the 1233zd used in connection with the present invention can be of either the trans or cis isomeric forms, and any and all combinations thereof, in preferred embodiments the 1233zd preferably comprises at least about 80%, or preferably at least about 90%, or preferably at least about 95%, or preferably at least about 97% of trans1233zd. In preferred embodiments, the 1233zd present in the formulation consists essentially of, or consists of, trans1233zd.

It is contemplated that the foaming agent can comprise a relative amount of 1233zd, and preferably trans1233zd, that varies widely depending on the specific performance parameters that are desired for any particular application. In preferred embodiments, the foaming agent comprises at least about 5% by weight of trans1233zd, and preferably from about 5% to about 100% of trans1233zd. The present invention also includes embodiments in which the foaming agent comprises a relative amount of 1233zd, and preferably trans11233zd, of from about 5% to about 60% of trans1233zd. The present invention also includes embodiments in which the foaming agent comprises a relative amount of 1233zd, and preferably trans1233zd, at least about 10% by weight of trans1233zd, or preferably from about 10% to about 100% of trans1233zd. The present invention also includes embodiments in which the foaming agent comprises from about 10% to about 60% of trans1233zd.

Non Post-Foaming Compositions. Formulations and Methods

As mentioned above, the present invention also includes creams, lotions, gels, foams, mists, powders, sprays and the like which do not exhibit post-foaming action. By way of example, the advantageous cooling effect as described herein can be provided for even creams, lotions, gels, foams, mists, powders, sprays and the like which are designed to not exhibit an post-foaming action but which nevertheless in which the 1233zd of the present invention evaporates after the creams, lotions, gels, foams, mists, powders, sprays and the like are applied to the skin, hair and/or mucous membrane of the user and thus provide the advantageous cooling effect as described herein. By way of further example, the advantageous ability of the present formulations, by virtue of inclusion in part of the 1233zd of the present invention, provides an advantageous ability of the active ingredient to penetrate into and/or be delivered directly into the skin/mucous membrane pores of the user and/or the hair follicles of the user even in embodiments in which post-foaming action is not achieved or desired.

Accordingly, the non-post-foaming embodiments of the present invention, can also utilize formulations and compositions in the form of creams, lotions, gels, foams, mists, powders, sprays and the like in which the formulations and compositions generally comprise: (a) one or more active components, preferably comprising a cleanser; (b) optionally but preferably one or more auxiliary components which help to form the creams, lotions, gels, foams, mists, powders, sprays and the like; (c) a foaming agent comprising, or consisting essentially of, or consisting of trans-1-chloro-3,3,3-trifluoropropene (1233zd(E)); and (d) optional additional components other than components (a), (b) and (c) that may be included in the composition. The types and amounts of components (a), (b) and (c) in such non-fost-foaming applications can vary broadly and include the types and amounts of such components as described herein in connection with post-foaming applications. In the non-post-foaming embodiments, for the purpose of convenience, but not by way of limitation, the components (a), (b) and (d) are also sometimes referred to herein as the "formulation base,"

or the "cleanser base" (in the case where the active component includes a cleanser) and the like.

PREFERRED EMBODIMENTS

A preferred embodiment of the present invention comprises from about 80% to about 99% of cleanser base and from about 1% to about 20% by weight of a foaming agent comprising, or consisting essentially of, or consisting of trans-1-chloro-3,3,3-trifluoropropene (1233zd(E), with said percentages being on a weight basis.

A preferred embodiment of the present invention comprises from about 80% to about 99% of cleanser base and from about 1% to about 20% by weight of a foaming agent, wherein the foaming agent comprises at least about 50% by weight of 1233zd(E), or at least about 75% by o weight f 1233zd(E), or at least about 80% by weight of 1233zd(E), or at least about 90% by weight of 1233zd(E), or at least about 100% weight based on all of the foaming agents in the composition.

A preferred embodiment of the present invention comprises from about 80% to about 99% of cleanser base and from about 1% to about 10% by weight of a foaming agent comprising, or consisting essentially of, or consisting of trans-1-chloro-3,3,3-trifluoropropene (1233zd(E), with said percentages being on a weight basis.

A preferred embodiment of the present invention comprises from about 50% to about 99% of cleanser base and from about 1% to about 50% by weight of a foaming agent, wherein the foaming agent comprises at least about 5% by of 1233zd(E), or at least about 10% by weight of 1233zd(E), or from about 5% by weight to about 50% by weight of 1233zd(E), or at least about 10% by weight to about 10% by weight to about 40% by weight of 1233zd(E) based on all of the foaming agents in the composition.

A preferred embodiment of the present invention comprises from about 90% to about 99% of cleanser base and from greater than 1% to less than about 10% by weight of a foaming agent, wherein the foaming agent comprises at least about 50% by weight of 1233zd(E) based on all of the foaming agents in the composition.

A preferred embodiment of the present invention comprises from about 90% to about 99% of cleanser base and from greater than 1% to less than about 10% by weight of a foaming agent, wherein the foaming agent comprises at least about 75% by weight of 1233zd(E) based on all of the foaming agents in the composition.

A preferred embodiment of the present invention comprises from about 90% to about 99% of cleanser base and from greater than 1% to less than about 10% by weight of a foaming agent, wherein the foaming agent comprises at least about 80% by weight of 1233zd(E) based on all of the foaming agents in the composition.

A preferred embodiment of the present invention comprises from about 90% to about 99% of cleanser base and from greater than 1% to less than about 10% by weight of a foaming agent, wherein the foaming agent comprises at least about 90% by of 1233zd(E) based on all of the foaming agents in the composition.

The present personal care compositions can be in the form of and/or used in a wide variety of personal care products/applications, including: shampoos (including baby shampoos, conditioning shampoos, moisturizing shampoos, etc.); skin and body cleansers (including shower gels, bath foams, facial cleansers, intimate cleansers, moisturizing body washes, antibacterial body washes; bath gels; hand soaps; facial scrubs; foot scrubs, etc); hair care compositions (including hair dyes, hair conditioners, hair creams and hair styling formulations); skin care compositions (including skin lotions, balms and creams, skin whiteners, self tanning lotions, sunscreen lotions, carrier lotions, moisturizers, vitamin C creams, antibacterial lotions, facial masks, body masks, make up foundations, sun care formulations, antiperspirants, etc).

EXAMPLES

Example 1—1233zd Foaming Agent

A self foaming gel (suitable for use as a shower gel and other personal care cleansers) 94 wt % cleanser base and 6 wt % 1233zd(E) was formed. This formulation is referred to herein as Gel 1.

Example 2—1233zd/Isopentane Azeotrope Foaming Agent

A self foaming gel (suitable for use as a shower gel and other personal care cleansers) comprising 94 wt % cleanser base and 6 wt % of an azeotrope-like mixture of 1233zd(E) and isopentane was formed. The azeotrope-like mixture consisted of 84% by weight of 1233zd(E) and 6% by weight of isopentane based on the 1233zd(E) and isopentane in the mixture. This formulation is referred to herein as Gel 2.

Comparative Example 1—Isopentane Foaming Agent

A self foaming gel comprising 96.7 wt % cleanser base and 3.3 wt % isopentane (representing the same mole % as was the case for 1233zd(E) in Gel C1. This formulation is referred to herein as Gel—C1.

Comparative Example 2—Isopentane Foaming Agent

A self foaming gel comprising 94 wt % cleanser base and 6 wt % isopentane was formed. This formulation is referred to herein as Gel C2.

Example 3—Wetting Capabilities

Each of Gel—1, Gel C1 were dispensed on paper, allowed to sit for 1 to 2 minutes and then smeared down the paper using a film applicator/draw-down bar. Photographs were then taken and are reproduced as FIG. 1A (front view) and FIG. 1B (back view).

Example 4—Spreading Capabilities

Figure 2:
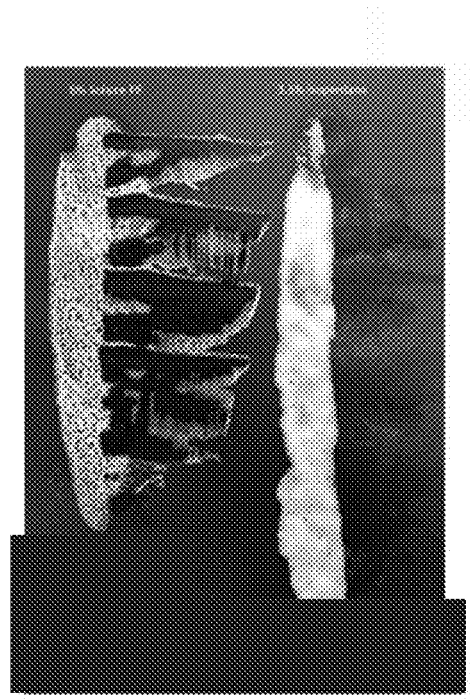
FIG. 2 is a black-and-white photograph showing the result from the experiment described in Example 4.

Each of Gel 1 and Gel C1 were dispensed on paper, allowed to sit for 1 to 2 minutes and then smeared down the paper using a film applicator/draw-down bar. The sample in each case was then smeared across the paper (horizontally) to expose the underlying paper. A photograph was then taken and is reproduced as FIG. 2.

Example 5—Spreading/Wetting Capabilities

Figure 3:
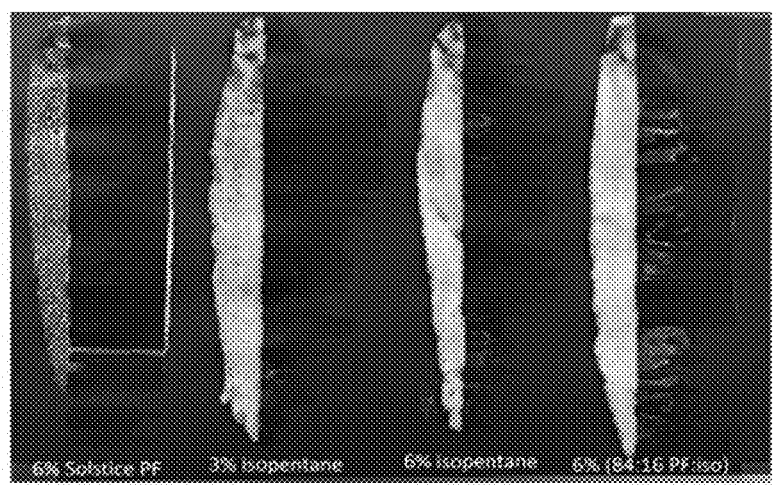
FIG. 3 is a black-and-white photograph showing the result from the experiment described in Example 5.

Each of Gel 1, Gel 2, Gel C1 and Gel C2 were dispensed on paper, allowed to sit for 1 to 2 minutes and then smeared down the paper using a film applicator/draw-down bar. The sample in each case was then smeared across the paper (horizontally) to expose the underlying paper. A photograph was then taken and is reproduced as FIG. 3.

This example shows the gels in accordance with the present invention (Gel 1 and Gel 2) exhibit superior wetting properties compared to gels made with hydrocarbons and alcohols (Gel C1 and Gel C2), thus having the substantial advantage of allowing skin/hair/body care products to penetrate better and further into the small pores of the skin, as well as resulting in better deposition of the active ingredients in and onto the skin/hair, which in turn results in better efficacy. Furthermore, the superior wetting properties provides improved spread ability, which in turn can result in increased contact area of the personal care product with the skin. These improved wettability and spreadability characteristics permit the possibility of achieving ethics the equivalent with prior products but using lower dosages/amounts of the product.

Example 6—Post Foaming Capabilities

Figure 4:
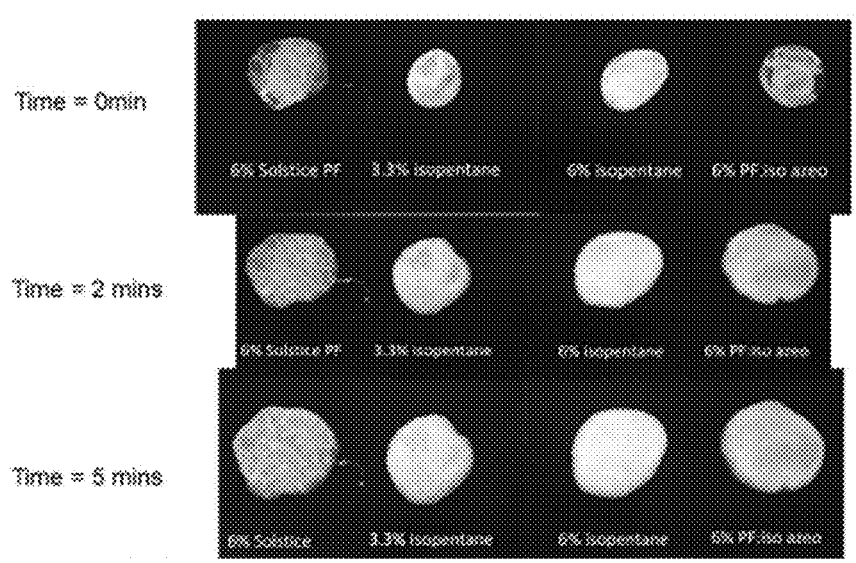
FIG. 4 is a black-and-white photograph showing the result from the experiment described in Example 6.

Each of Gel 1. Gel 2. Gel C1 and Gel C2 were evaluated for foaming properties. Photographs were then taken and are reproduced as FIG. 4.

The results of this test show that gels formed in accordance with the present invention (Gel 1 and Gel 2) show a highly advantageous and unexpected delayed post—foaming action which includes the benefit of enabling better spreading of the product on the skin/scalp before the foaming action begins. In addition, this property allows carrying and settling of formulations having higher viscosity which in turn has the benefit of providing an improved (e.g., cushiony) feel in comparison to foams made with hydrocarbons alcohols, which have the disadvantage of essentially instantaneously producing an instant thin foamy product on the skin/scalp. Delayed foaming properties can also have the advantage of providing a visual indication to the user that the product is continuing to work over a longer period of time.

Example 7—Cooling Longevity

Figure 5:
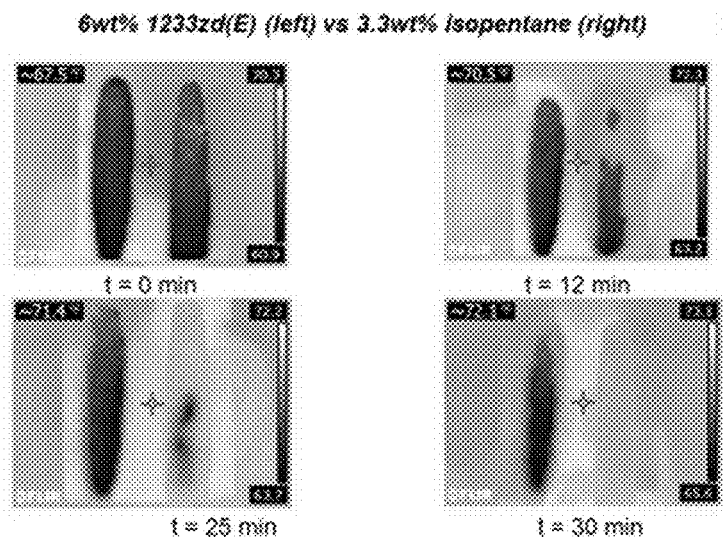
FIG. 5 is a color photograph showing the result from the experiment described in Example 7.

Each of Gel 1 and Gel C1 were dispensed on paper, allowed to sit for 30 minutes, with infrared photographs taken at 0 minutes, 12 minutes, 25 minutes and 30 minutes after application. These photographs are provided as FIG. 5. These images, which show by the presence of dark areas (colored purple in the color photographs) ongoing cooling effect as a function of time after application, clearly indicate that as long as 30 minutes after application the cooling effect continues in accordance with the gels of present invention whereas gels made with previously used hydrocarbons (isopentane) have a deteriorated cooling effect after 12 minutes with cooling substantially discontinued after about 25 minutes.

Example 8A—Cooling Longevity

Figure 6:
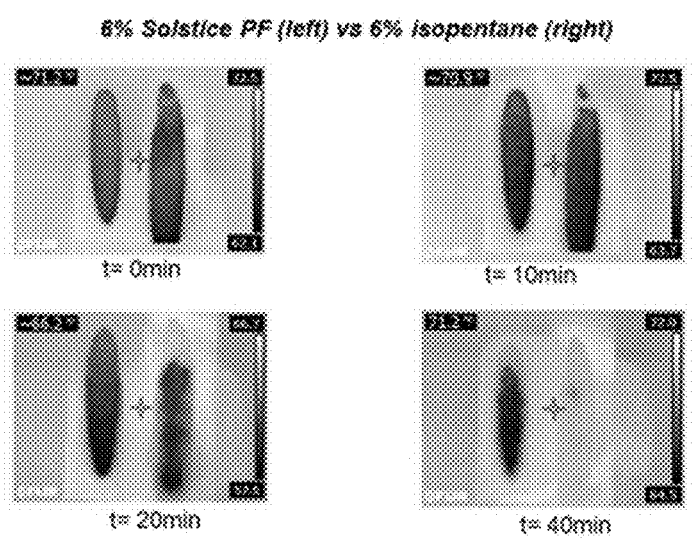
FIG. 6 is a color photograph showing the result from the experiment described in Example 8A.

Each of Gel 1, Gel C1 and Gel C2 were dispensed on paper under ambient conditions (approximately 72 F), allowed to sit for 40 minutes, with infrared photographs taken at 0 minutes. 10 minutes, 20 minutes and 40 minutes after application. These photographs are provided as FIG. 6. These images, which show by the presence of dark areas (colored purple in the color photographs) ongoing cooling effect as a function of time after application, clearly indicate that as long as 40 minutes after application the cooling effect continues in accordance with the Gels of present invention whereas gels made with previously used hydrocarbons (isopentane) have a deteriorated cooling effect after 20 minutes with cooling substantially discontinued by 40 minutes.

For each of Gel 1 and Gel C2, the weight of gel applied (initial application weight) is determined. The weight of the amounts remaining on the paper at post-application times of 5 minutes, 10 minutes, 15 minutes, 20 minutes and 25 minutes were then determined. The results are provided in Table 1 below:

TABLE 1

| Time after application (min.) | Weight Percent Remaining | | |
|---|---|---|---|
| | Gel 1 (6% 1233zd(E)) | Gel C2 (6% isopentane) | Gel C1 (3.3% isopentane) |
| 5 | 88.4 | 80.7 | 82.9 |
| 10 | 79.7 | 66.7 | 72.4 |
| 15 | 71.0 | 56.1 | 63.2 |
| 20 | 63.8 | 45.6 | 53.9 |
| 25 | 56.5 | 38.6 | 47.4 |

The results reported in table 1 above show surprising and unexpected advantage in accordance with the present invention in that Gel 1 leave the paper at a much slower rate than the rate at which an equivalent amount by weight of isopentane leaves the paper. Although applicants do not intend to be bound by or to any particular theory of operation, it is believed that this unexpected result contributes at least in part to the unexpected longevity of the cooling effect provided in accordance with the gels of the present invention. This result is especially unexpected given that the boiling point of 1233zd(E) is lower than the boiling point of isopentane.

Example 8B—Cooling Longevity

Each of Gel 2. Gel C1 and Gel C2 were dispensed on paper under ambient conditions (approximately 72 F) and the weight of gel applied (initial application weight) is determined. The amounts by weight of the amount of the gel remaining on the paper at post-application times of 5 minutes, 10 minutes, 15 minutes, 20 minutes and 25 minutes were then determined. The results are provided in Table 2 below:

TABLE 2

| Time after application (min.) | Weight Percent Remaining | | |
|---|---|---|---|
| | Gel 2 (6% azeotrope of 1233zd(E) + isopentane) | Gel C2 (6% isopentane) | Gel C1 (3.3% isopentane) |
| 5 | 83.3 | 80.7 | 82.9 |
| 10 | 72.2 | 66.7 | 72.4 |
| 15 | 62.5 | 56.1 | 63.2 |
| 20 | 55.6 | 45.6 | 53.9 |
| 25 | 48.6 | 38.6 | 47.4 |

Example 9—1233zd Foaming Agent

A self foaming gel (suitable for use as a shower gel and other personal care cleansers) comprising 97 wt % cleanser base and 3 wt % 1233zd(E) was formed. This formulation is referred to herein as Gel 9.

Example 10—1233zd Foaming Agent

A self foaming gel (suitable for use as a shower gel and other personal care cleansers) comprising 90 wt % cleanser base and 10 wt % 1233zd(E) was formed. This formulation is referred to herein as Gel 10.

Example 11—Cooling Longevity

Figure 7:
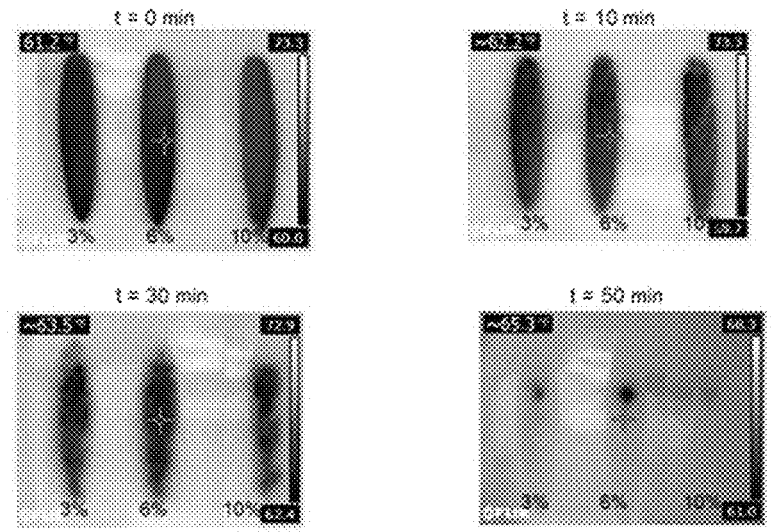
FIG. 7 is a color photograph showing the result from the experiment described in Example 11.

Each of Gel 9, Gel 1 (6% 1233zd(E)) and Gel 10 were dispensed on paper, allowed to sit for 50 minutes, with infrared photographs taken at 0 minutes, 10 minutes, 30 minutes and 50 minutes after application. These photographs are provided as FIG. 7. The attached data shows that cooling longevity occurs in accordance with the present invention for concentrations of 1233zd(E)) at each of three, six and 10% since in each case the color purple shows cooling effect even 30 minutes after application. Moreover, and further unexpectedly, the data shows that the cooling effect is desirably enhanced for concentration ranges of 3 to 6% (as shown by the deep dark purple color) initially and at 10 minutes after application in addition, some cooling effect continues even at 50 minutes with concentrations from about three to about 6%, whereas at a concentration of about 10% the cooling effect is substantially dissipated.

Comparative Example 3—No Foaming Agent

A gel comprising 100% of the same cleanser base as Comparative Example 1 is formed, that is, with no foaming agent. This formulation is referred to herein as Gel—C3.

Comparative Example 4—1% 1233zd(E) Foaming Agent

A gel comprising 99 wt % cleanser base and 1 wt % 1223zd(E) was formed. This formulation is referred to herein, for comparison to formulations containing greater than 1% 1233zd(E), as Gel C4.

Figure 8:
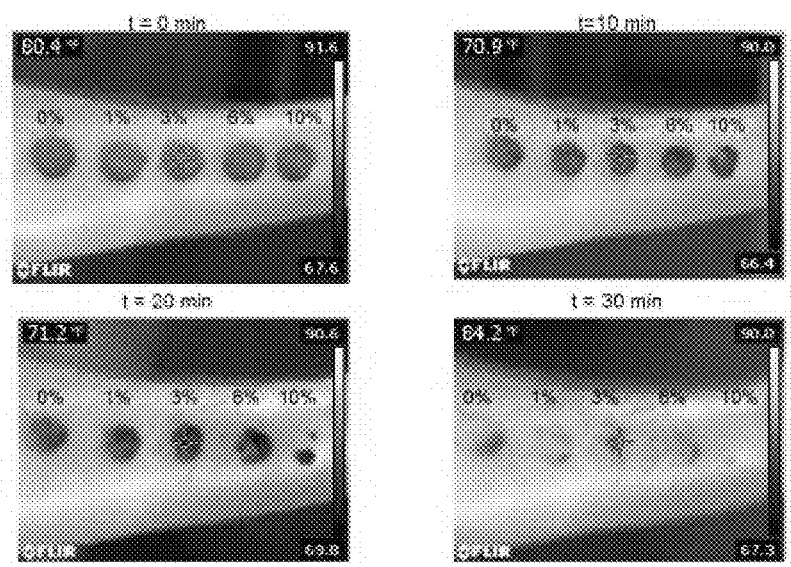
FIG. 8 is a color photograph showing the result from the experiment described in Example 12

Example 12—Cooling Longevity 2 grams of each of Gel—C3 (i.e., 0% 1233zd), Gel—C4 Gel 1 (i.e., 1% 1233zd). Gel 9 (3% 1233zd), Gel 1 (6% 1233zd), and Gel C1 (10% 1233zd) were dispensed onto the inner forearm of a human subject (with ambient temperature of 72° F.) and rubbed at essentially the same time and the same manner into a circular application on the skin and allowed to sit for 30 minutes, with infrared photographs taken at 0 minutes, 10 minutes, 20 minutes and 30 minutes after application. These photographs and are provided in FIG. 8.

Based on this Example 12 it is concluded that exceptional and unexpected longevity of cooling sensation is provided at concentrations of greater than 1% by weight to less than about 10% by weight of 1233zd, as illustrated in the photograph series above by the darkest color being produced at these concentrations, with concentrations of from about 3% to about 6% produces the most unexpected and the most superior results. No irritation or negative feeling to the user was produced.

What is claimed is:

1. A method of treating human skin, hair and/or mucous membranes comprising:
    (a) providing a personal care composition in the form of a gel, lotion or cream comprising: (i) one or more active ingredients; (ii) optionally one or more auxiliary gel, lotion or cream forming components; and (iii) foam forming component(s) consisting essentially of trans-1-chloro-3,3,3-trifluoropropene (1233zd(E));
    (b) spreading said gel, lotion or cream on and/or into the skin, haft and/or mucous membrane of the human being treated; and
    (c) foaming said gel, lotion or cream during delivery and/or while in contact with the skin, hair and/or mucous membrane by evaporating said trans-1-chloro-3,3,3-trifluoropropene (1233zd(E)) from said gel, lotion or cream.

2. The method of claim 1 wherein said personal care composition comprises one or more auxiliary gel, lotion or cream forming components.

3. The method of claim 1 wherein said proving step comprises providing said gel, lotion, or cream in a container.

4. The method of claim 3 wherein said foaming step comprises spreading said gel, lotion, cream and/or foam on and/or into the skin, haft and/or mucous membrane of the human being treated and wherein said foaming provides an extended cooling effect to the user.

5. The method of claim 4 wherein said foaming step comprises spreading said gel, lotion, cream and/or foam on and/or into the skin, hair and/or mucous membrane of the human being treated and wherein said spreading provides energy for said evaporation of said 1233zd(E).

6. The method of claim 5 wherein said container is under pressure.

7. The method of claim 1 wherein said personal care composition further comprises trans-1,3,3,3-tetrafluoropropene (1234ze (E)).

8. A personal care formulation for treating human skin, hair and/or mucous membranes comprising a gel, lotion, or cream comprising:
    (a) one or more active ingredients for providing a beneficial effect to the skin and/or haft and/or mucous membranes of a human,
    (b) optionally one or more auxiliary gel, lotion or cream forming components, and
    (c) at least about from about 1 percent by weight to about 50 percent by weight based on the total of components (a), (b) and (c) of foam forming component(s), wherein said foam forming component comprises at least about 75% by weight of trans-1-chloro-3,3,3-trifluoropropene (1233zd(E)).

9. The personal care composition of claim 8 comprising from about 1 percent by weight to about 10 percent of said foam forming components.

10. The personal care composition of claim 9 wherein said foam forming components consist essentially of said 1233zd (E).

11. The personal care composition of claim 9 wherein said foam forming components consist of said 1233zd(E).

12. The personal care composition of claim 9 comprising from about 3 percent by weight to about 6 percent of said foam forming components based on the weight of the components in the personal care composition and wherein said foam forming component(s) comprise at least about 90% by weight of said 1233zd(E).

13. The personal care composition of claim 9 wherein said foam forming components consist essentially of from about 3 percent by weight to about 6 percent of said 1233zd(E) based on the weight of the components in the personal care composition.

14. The personal care composition of claim 9 wherein said foam forming components consist of from about 3 percent by weight to about 6 percent of said 1233zd(E) based on the weight of the components in the personal care composition.

15. A method of treating human skin, hair and/or mucous membranes with a personal care gel, lotion, cream or foam, said method comprising:
- (a) providing a closed container openable to dispensing the contents thereof and including therein a personal care formulation in the form of an emulsion and/or dispersion comprising:
  - (i) one or more active ingredients for providing a beneficial effect to the skin and/or hair of a human,
  - (ii) optionally one or more auxiliary gel, lotion, or cream forming components,
  - (iii) foam forming component(s) present in an amount of from about 30 percent by weight to about 50 percent by weight based on the total weight of the components (i), (ii) and (iii), said foam forming component(s) comprising:
    - (1) at least about 90 percent by weight, based on the total of components (1) and (2), of trans-1-chloro-3,3,3-trifluoropropene (1233zd(E)); and optionally
    - (2) a co-foaming agent different than said 1233zd(E); and
  - (iv) optionally an external propellant for providing a force tending to eject said personal care composition from said container,
- (b) dispensing said personal care formulation from said container by propelling said personal care formulation from said container;
- (c) applying said dispensed personal care formulation to the skin, hair and/or mucous membranes; and
- (d) providing a cooling sensation to the human being treated by evaporating at least a portion said trans-1-chloro-3,3,3-trifluoropropene (1233zd(E)) from said applied personal care composition after said dispensing step.

16. The method of claim 15 wherein said dispensing step initiates foaming of said personal care formulation.

17. The method of claim 16 wherein said co-foaming agent is present.

18. The method of claim 17 wherein said applying comprises spreading said personal care composition onto the user and wetting the skin, hair and/or mucous membrane of the user while said cooling sensation is being provided to the user.

* * * * *